United States Patent
Powell (10) Patent No.: US 7,483,139 B2
(45) Date of Patent: Jan. 27, 2009

(54) SMOKE DETECTOR

(75) Inventor: Brian Powell, Maidenhead (GB)

(73) Assignee: Kidde IP Holdings Limited (GB)

( * ) Notice: Subject to any disclaimer, the term of this patent is extended or adjusted under 35 U.S.C. 154(b) by 400 days.

(21) Appl. No.: 10/515,883

(22) PCT Filed: May 15, 2003

(86) PCT No.: PCT/GB03/02121

§ 371 (c)(1), (2), (4) Date: Nov. 24, 2004

(87) PCT Pub. No.: WO03/100397

PCT Pub. Date: Dec. 4, 2003

(65) Prior Publication Data

US 2005/0173638 A1      Aug. 11, 2005

(30) Foreign Application Priority Data

May 27, 2002  (GB) ................... 0212171.3

(51) Int. Cl.
*G01N 21/00* (2006.01)
(52) U.S. Cl. ................ 356/438; 356/437
(58) Field of Classification Search ............ None
See application file for complete search history.

(56) References Cited

U.S. PATENT DOCUMENTS

| | | | |
|---|---|---|---|
| 3,869,208 A | | 3/1975 | Lorenz |
| 3,994,603 A | * | 11/1976 | Paschedag ............ 356/438 |
| 4,221,485 A | * | 9/1980 | Schulze ................ 356/338 |
| 4,547,675 A | * | 10/1985 | Muggli et al. ........ 356/438 |
| 4,711,571 A | | 12/1987 | Schuman |
| 4,857,895 A | | 8/1989 | Kaprelian |
| 4,942,305 A | | 7/1990 | Sommer |
| 5,220,179 A | * | 6/1993 | Gagea ................... 356/438 |
| 5,381,130 A | * | 1/1995 | Thuillard et al. ..... 356/438 |
| 5,392,114 A | * | 2/1995 | Cole .................... 356/341 |

(Continued)

FOREIGN PATENT DOCUMENTS

CH      607 687      10/1978

(Continued)

*Primary Examiner*—Gregory J Toatley, Jr.
*Assistant Examiner*—Juan D Valentin
(74) *Attorney, Agent, or Firm*—Merchant & Gould P.C.

(57) ABSTRACT

A smoke detector (1) has a spherical chamber (2) including a plurality of holes (15,17) for allowing smoke and other particles to enter the chamber. The majority of the internal surface (3) of the chamber (2) is covered with a high reflectivity Lambertian surface, that is a material that scatters incident light equally in all directions and at all wavelengths. The remaining portion of the internal surface (3) is coated with a light absorbing material (13) such as a matt black coating. A scatter sensor (9) is directed towards the absorbing coating (3), and an integrating detector (5) is configured to detect radiation directly from the entire Lambertian surface. A first LED (19) emits blue light into the chamber (2), and a second LED (21) emits infrared light into the chamber. Processing means (23, 25 and 27) are provided to analyse the signals from the detectors (5,9), including means for discriminating between signals from the sensors indicative of different frequencies of received radiation. The processing means can distinguish between different smoke types, such as white/grey smoke and black smoke, and can also distinguish between smoke and other particles.

33 Claims, 9 Drawing Sheets

U.S. PATENT DOCUMENTS

| | | |
|---|---|---|
| 5,491,336 A | 2/1996 | Concannon et al. |
| 6,225,910 B1 | 5/2001 | Kadwell et al. |
| 6,326,897 B2 | 12/2001 | Kadwell et al. |
| 6,396,405 B1 * | 5/2002 | Bernal et al. ............. 356/438 |
| 6,469,623 B2 * | 10/2002 | Pattok et al. ............. 340/516 |
| 6,535,278 B1 * | 3/2003 | Imura ..................... 356/73 |
| 6,603,555 B1 * | 8/2003 | Nanami et al. ............ 356/437 |
| 6,788,211 B2 * | 9/2004 | Kouznetsov et al. ....... 356/438 |
| 7,023,913 B1 * | 4/2006 | Monroe ................. 375/240.01 |
| 7,048,068 B2 * | 5/2006 | Paulkovich .............. 340/578 |
| 2001/0020899 A1 | 9/2001 | Kadwell et al. |

FOREIGN PATENT DOCUMENTS

| | | |
|---|---|---|
| DE | 196 10 438 | 10/1996 |
| EP | 1 508 032 B1 | 8/2007 |
| GB | 2 141 553 | 12/1984 |
| GB | 2 319 604 | 5/1998 |
| GB | 2 330 410 | 4/1999 |
| SE | 607 687 | 10/1978 |

* cited by examiner

SMOKE DETECTOR

TECHNICAL FIELD

The present invention relates to particle detectors and to a method of detecting particles—particularly, but not exclusively, smoke particles.

BACKGROUND ART

There are two detector types for detecting such particles. Obscuration, or direct, detectors have an emitter of suitable electromagnetic radiation, such as visible light, aligned with a detector for the radiation such that a beam of the radiation generated by the emitter shines directly into the detector through a volume in which the particles may be present. This type of detector thus measures the radiation lost from the beam, along a known path-length, across the volume containing the smoke, and is commonly measured as %/m of radiation lost. The radiation is lost from the beam by a combination of reflection, scattering and absorption in the smoke particles. Obscuration detectors typically work well for black smoke but are less sensitive to white or grey smoke. Additionally, obscuration detectors typically are not housed within a chamber, as they have an emitter and a detector spaced at a substantial distance, such as 1 m, to provide adequate sensitivity.

Indirect or reflected detectors, commonly called scattering detectors, have an emitter and detector positioned on non-colinear axes such that the radiation from the emitter does not shine directly onto the detector. Smoke particles reflect or scatter light from the emitter into the receiver. Scattering detectors generally work well for white or grey smoke but have a decreased sensitivity to black smoke.

In white or grey smoke, for example from smouldering materials, reflection and scattering dominate and both these processes contribute to the signal produced by the scattering detector, and therefore the scatter signals are relatively strong for this type of smoke relative to an obscuration signal that would be produced by an obscuration detector. With black smoke, such as generated by flaming hydrocarbon fuels or burning plastics, most of the radiation is lost by absorption in the smoke particles and this absorbed light does not contribute to the scattered light signal produced by the scattering detector, and therefore the scattered light signal of a scattering detector is relatively small with this type of smoke compared to the signal generated by an obscuration detector.

Obscuration detectors that make a measurement of light transmission through the smoke are used extensively in beam smoke detectors but not in point smoke detectors because the path lengths available are relatively short, without complicated optical arrangements which can be prone to contamination, and this places great demands on the stability of the measurement. For instance, to obtain a sensitivity of 10%/m over a path length of 10 cm, a transmitted signal change of 1% would have to be detected.

U.S. Pat. No. 4,857,895 discloses a smoke detector having a double pass absorption path across an enclosed volume achieved by a lens or mirror. A second detector, placed at an approximate right angle to the beam, detects the scattered light. The intention of the device is to increase the black smoke sensitivity. There is also provision for separate light sources for the obscuration measurement and for the scatter measurement and it is disclosed that a green LED provides better obscuration sensitivity whereas the scatter LED can be a conventional infrared LED. Alarm is generated by either the scatter or obscuration signal passing through simple thresholds or, alternatively, if the difference in the two signals exceeds a threshold.

U.S. Pat. No. 6,225,910 and U.S. Patent Application No. 2001 020899 also disclose obscuration devices and scattering devices in the same housing. The two documents disclose various optical arrangements to increase the obscuration path length. The arrangements involve single and multiple specular reflections from a mirror or mirrors. There is also the provision in U.S. Pat. No. 6,225,910 for the obscuration measurement to be in the blue/green and the scatter measurement to be in the infrared.

DISCLOSURE OF INVENTION

According to the present invention, there is provided a particle detector including a chamber for receiving particles, radiation emitting means for emitting radiation into the chamber, and radiation detecting means for detecting radiation within the chamber, wherein the chamber includes a substantially high reflectivity Lambertian surface.

According to a further aspect of the invention, there is provided a particle detecting method including the steps of providing a chamber for receiving particles and having a substantially high reflectivity Lambertian surface, emitting radiation into the chamber, and detecting radiation within the chamber.

In embodiments to be described, the chamber is an integrating sphere. This is a spherical cavity into which light or other radiation is directed. The internal surfaces of the cavity are coated with as, near as possible, a high reflectivity (for example, greater than 90%) Lambertian scattering material, that is a material that efficiently scatters incident light equally in all directions at all wavelengths. The material commonly used is barium sulphate but most matt white paints are approximately Lambertian. A detector views the internal surface of the sphere but not the source directly, and therefore light reaching the detector has followed a multiplicity of paths within the sphere and has probably been scattered several times from the walls before reaching the detector. If absorbing particles (such as black smoke) are introduced into the sphere, the detected signal is reduced. Conversely, if scattering particles (such as white/grey smoke) are introduced into the sphere, the scattered light is not lost and should eventually reach the detector. There is thus produced a point smoke detector in which the output (the integrated signal from the detector) is sensitive to black smoke but relatively insensitive to white/grey smoke, which is the opposite of standard scattering detectors.

One advantage of the integrating sphere of the embodiments being described is that several different light sources can be mounted in the sphere at relatively arbitrary positions, allowing measurements to be made at two or more wavelengths with one detector by frequency or time division multiplexing. Also, there are no critical alignments in the system and the scattering surface is substantially all of the internal surface of the sphere, so it should be relatively insensitive to localised contamination.

A potential disadvantage of the integrating sphere arrangement is its relative insensitivity to white/grey smoke. However, in the embodiments being described, this is mitigated by the addition of a second detector mounted in or on the internal surface of the chamber, which is arranged so that it is mainly sensitive to scattered light (that is, it is not directly aligned with the radiation source(s)). The addition of this detector compromises the performance of the integrating sphere to some extent, as the part of the surface of the sphere that this detector views is made black to reduce the background signal, in the absence of smoke, to a manageable level. However, holes must also be included in the sphere to allow smoke to enter and it is advantageous to locate these holes in the black part of the sphere to minimise the disturbance to the integrating sphere.

BRIEF DESCRIPTION OF THE DRAWINGS

For a better understanding of the present invention, an embodiment thereof will now be described by way of example, with reference to the accompanying drawings, in which.

MODE OF CARRYING OUT THE INVENTION

Figure 1:
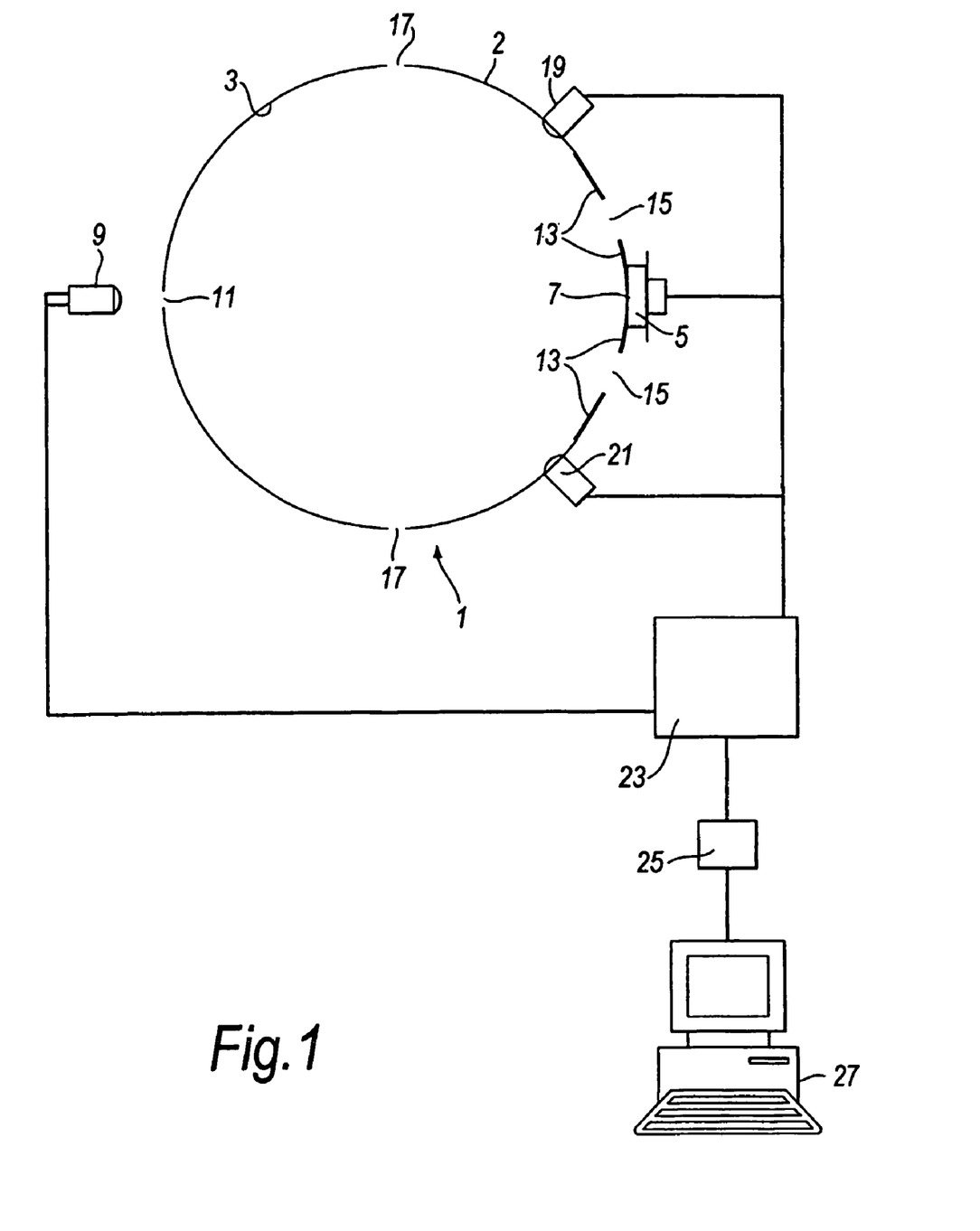
FIG. 1 is a schematic cross-sectional view of a smoke detector according to the invention.

The smoke detector 1 comprises a hollow sphere 2 machined from aluminium alloy (or other suitable material) with an internal diameter in this example of 50 mm. Most of the internal surface 3 of the detector 1 is coated with a material in order to provide the surfaces so coated with a substantially high reflectivity (greater than 90%) Lambertian surface. A suitable material is barium sulphate. An integrating detector 5, for example a Centronic OSD5-1T silicon photodiode of 5 mm$^2$ sensitive area, mounted on the exterior surface of the sphere 2, views a large portion of the white, inner surface 3 through a 5 mm diameter aperture 7. A scattering detector 9, for example an NSL710 silicon photodiode, is mounted on the exterior surface of the sphere 2 opposite the integrating detector 5 and is lensed so that it has a restricted viewing angle through aperture 11. A black painted region 13 of the internal surface of the sphere surrounds the integrating detector 5. One suitable black paint has the trade name Nextel and is manufactured by Mankiewicz Gebr. and Co. in Germany. This region 13 also contains six 5 mm diameter holes 15 to allow smoke access to the spherical cavity. There are also additional holes 17 at 90° from the integrating detector to allow flow through the cavity.

Two 5 mm diameter, plastic encapsulated LEDs 19,21 are mounted in apertures in the sphere 2 at 45° from the integrating detector 5 position. One is an RS 235-9922 470 nm blue LED 19, which is lensed such that it has a + or −15° beam spread. The second is a Siemens LD274-3 950 nm infrared LED 21, which is lensed to give a + or −10° beam spread. The beam spread of the LEDs 19,21 is thought not critical for the integrating measurement but is more important for the scattered light measurements. The radiation from the LEDs 19,21 is absorbed, reflected and scattered by smoke and other particles.

It should be understood that, instead of two radiation sources of different wavelength ranges, a single radiation source could be used, or three or more radiation sources, each having a different wavelength range, could be used.

Figure 2:
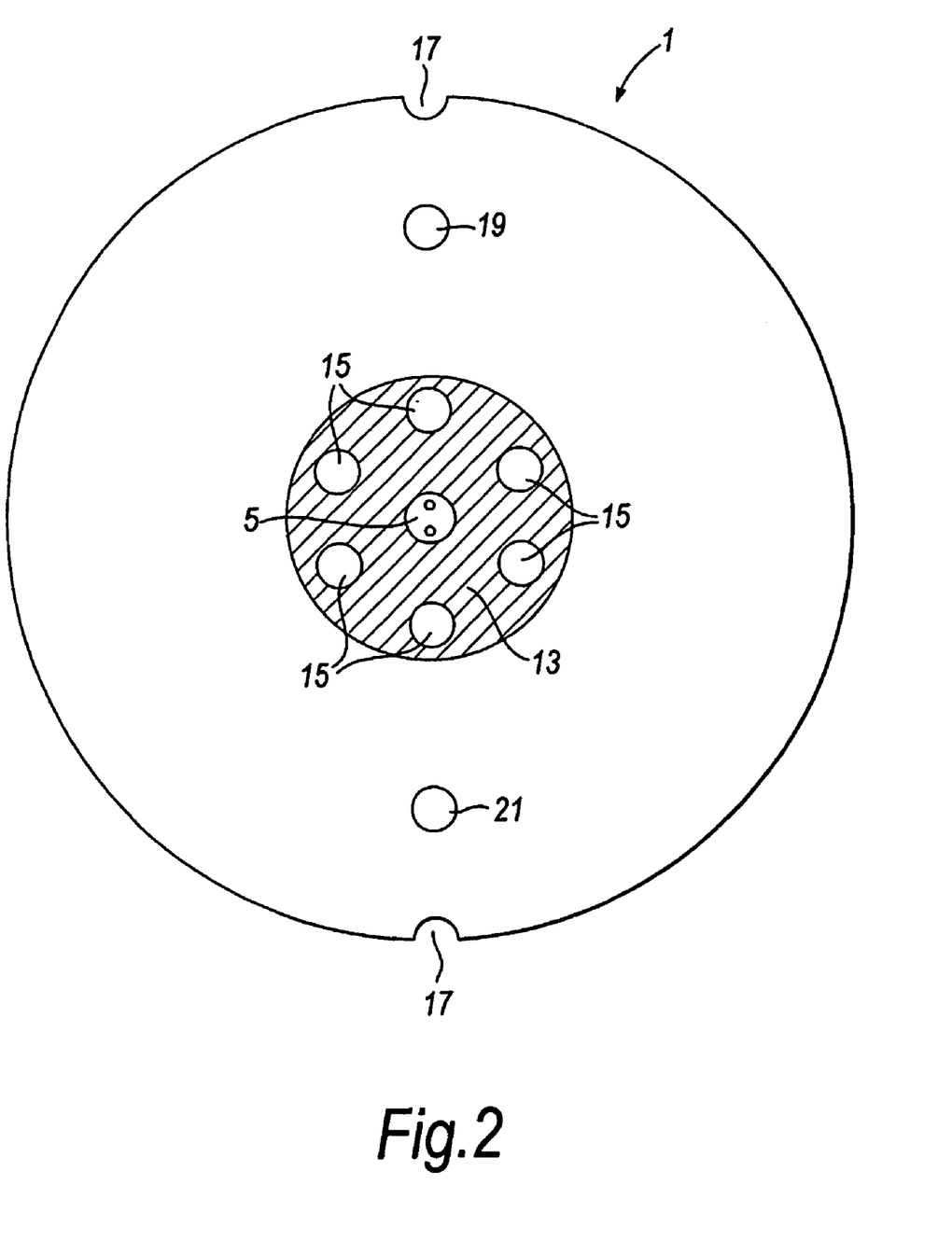
FIG. 2 is a side plan view of the smoke detector of FIG. 1.

FIG. 2 shows a view of the detector 1 from the end in which the integrating detector 5 is mounted. The black painted region 13 is shown as a dotted area in this figure, although it is, of course, not visible from the exterior of the detector 1.

The chamber of the detector could be of a form other than spherical—for example ellipsoidal. The chamber advantageously has a shape such that the integrating detector 5 can be positioned in a wall thereof such that it can view directly a large part of the Lambertian surface.

The LEDs 19,21 are driven by drive circuits in control means 23 (FIG. 1) at different frequencies. The signals from the two detectors 7,9 are amplified by control means 23 and the four signals, blue and infrared integrated signals and blue and infrared scattered signals, are obtained from four lock-in amplifiers in control means 23. These are in two pairs, the two amplifiers in each pair are supplied with a reference signal from each of the LED drive circuits. The input from one pair of lock-in amplifiers is taken from the integrating detector amplified output and the input to the other pair from the scatter detector amplified output. For example, in one implementation, the LEDs 19, 21 are driven at different frequencies of about 1 kHz, 50% duty cycle at a current of 20 mA, for the blue LED 19, and 30 mA for the infrared LED 21.

The smoke detector 1 has been tested with smoke and other aerosols in a UL217 smoke test box (Underwriters Laboratories Inc. Standard for Safety, Single and Multiple Station Smoke Alarms, Fifth Edition, 21 Feb. 1997). This was fitted with two obscuration meters; one, according to UL217, which worked in the visible region of the electromagnetic spectrum and which is referred to as the visible obscuration meter, and one, according to EN54 (BS5445: Part 7: 1984), which operated at 880 nm and which is referred to as the infrared obscuration meter. The tests described below were carried out using a Lambertian surface (on the internal surface 3 of the detector 1) formed by painting the internal surface 3 with white water-soluble Tipp-Ex (registered trade mark) correction fluid. This gives a fairly good, dense white coating. However, it is not very permanent and a better coating would be provided for a practical device by using a material such as barium sulphate.

Smoke was generated from various smouldering and flaming materials. Non-smoke aerosols were also generated, such as a condensed water mist produced from a domestic wallpaper stripper, dust and aerosol spray cans. The airflow velocity, produced by the circulation fan, was set to 0.15 m/s (30 fpm).

The detector output, together with the obscuration meter data, was recorded via an ADC (analogue to digital converter) board 25 in a desk-top computer 27 controlled by Testpoint software. The data was recorded to file for subsequent analysis. Recording was started and the smoke source introduced after 10 to 20 s. The smoke density was allowed to increase until the smoke source was exhausted when the smoke density was allowed to stabilise for a short period before the exhaust fan was turned on. Recording was continued until the obscuration meter readings had returned to a value close to zero.

Figure 3A:
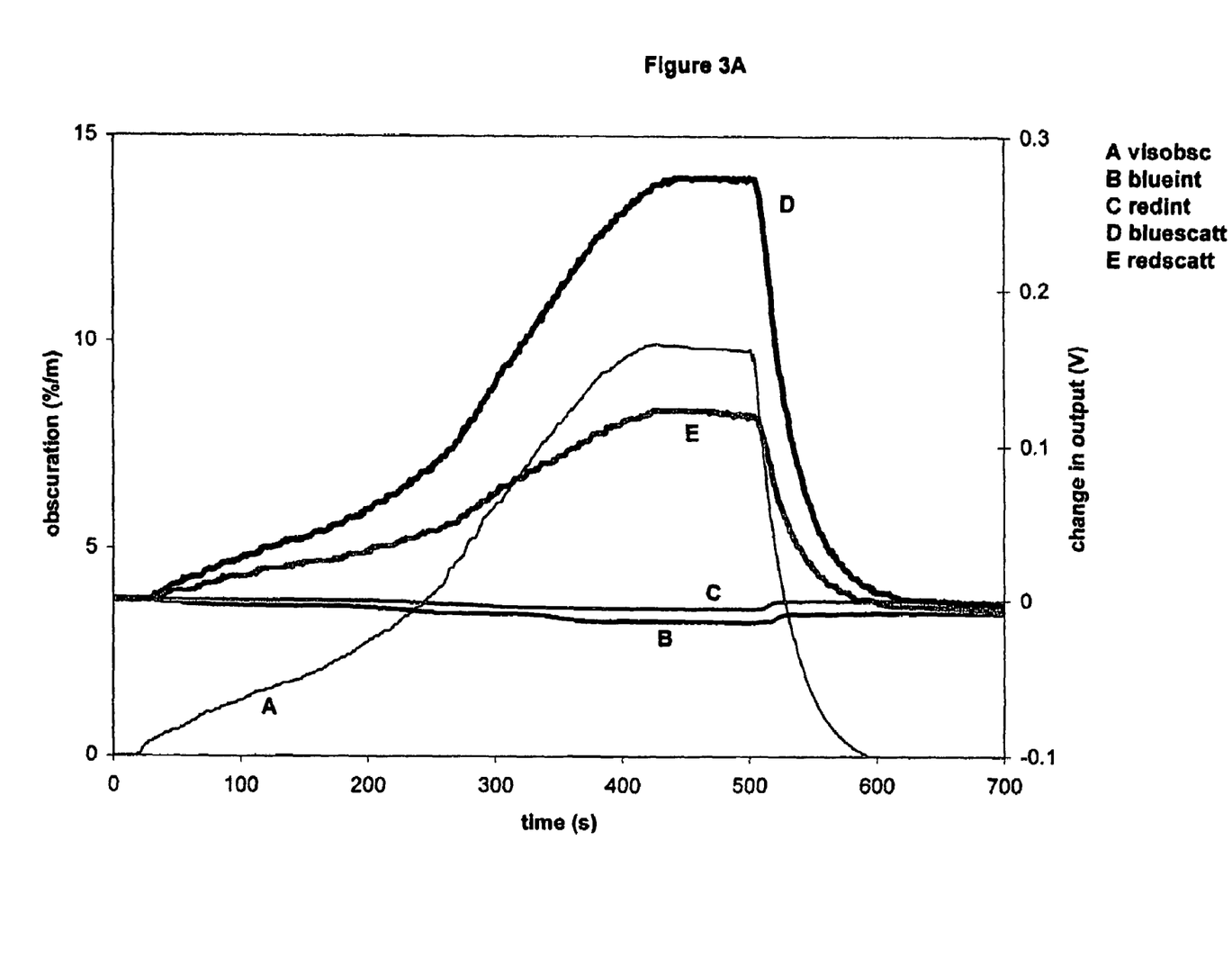
FIG. 3A is a graph showing the change in the blue and infrared signals from the integrating and scattering detectors, compared to the visible obscuration, for white smoke generated from smouldering cotton.
Figure 4A:
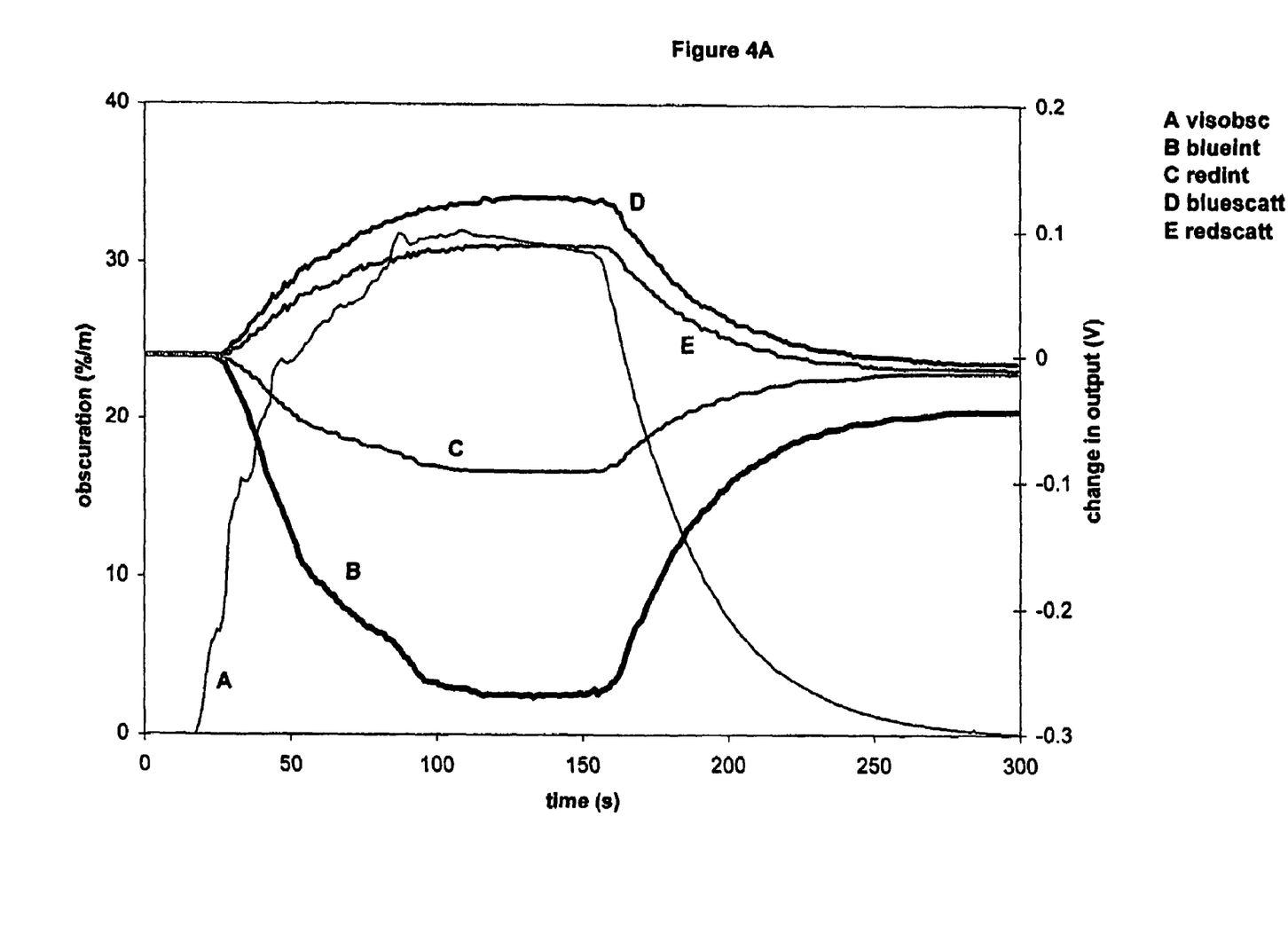
FIG. 4A is a graph showing the change in the blue and infrared signals from the integrating and scatter detectors, compared to the visible obscuration, for black smoke generated from flaming polystyrene.

Typical results obtained from white smoke, produced by smouldering cotton, and black smoke, produced by flaming polystyrene, are shown respectively in FIGS. 3A and 4A. In these Figures, the change in the four output signals, in volts, is plotted against the right hand axis. The corresponding visible obscuration meter reading, in %/m, is plotted against the left hand axis.

In the graphs of FIGS. 3A, 3B, 4A, 4B, 5 and 6, the plotted lines show the following output signals:—
  visobsc: visible light obscuration meter reading.
  IRobsc: infrared obscuration meter reading.
  blueint: blue integrated signal.
  redint: red integrated signal.
  bluescatt: blue scattered signal.
  redscatt: red scattered signal.

It can be seen, from FIG. 3A, that the introduction of white smoke has little effect on the integrating detector 5 output, whereas the scattering detector 9 responds to the presence of smoke well. There is a delay, of approaching 10s, between the obscuration meter response and the detector response because the smoke is generated close to the obscuration meters and there is a transit delay before the smoke reaches and penetrates the detector.

The response to black smoke, generated in this example from flaming polystyrene, shown in FIG. 4A, was markedly different with a strong response from the integrating detector 5 and a smaller response, with respect to the obscuration meter, from the scattering detector 9.

In both the black and white smoke cases and for both detectors, the response of the blue signal was greater than the response of the infrared signal. The relative magnitude of the signals, in both cases, was a function of the LED drive currents and the gains in the two-amplifiers.

Figure 3B:
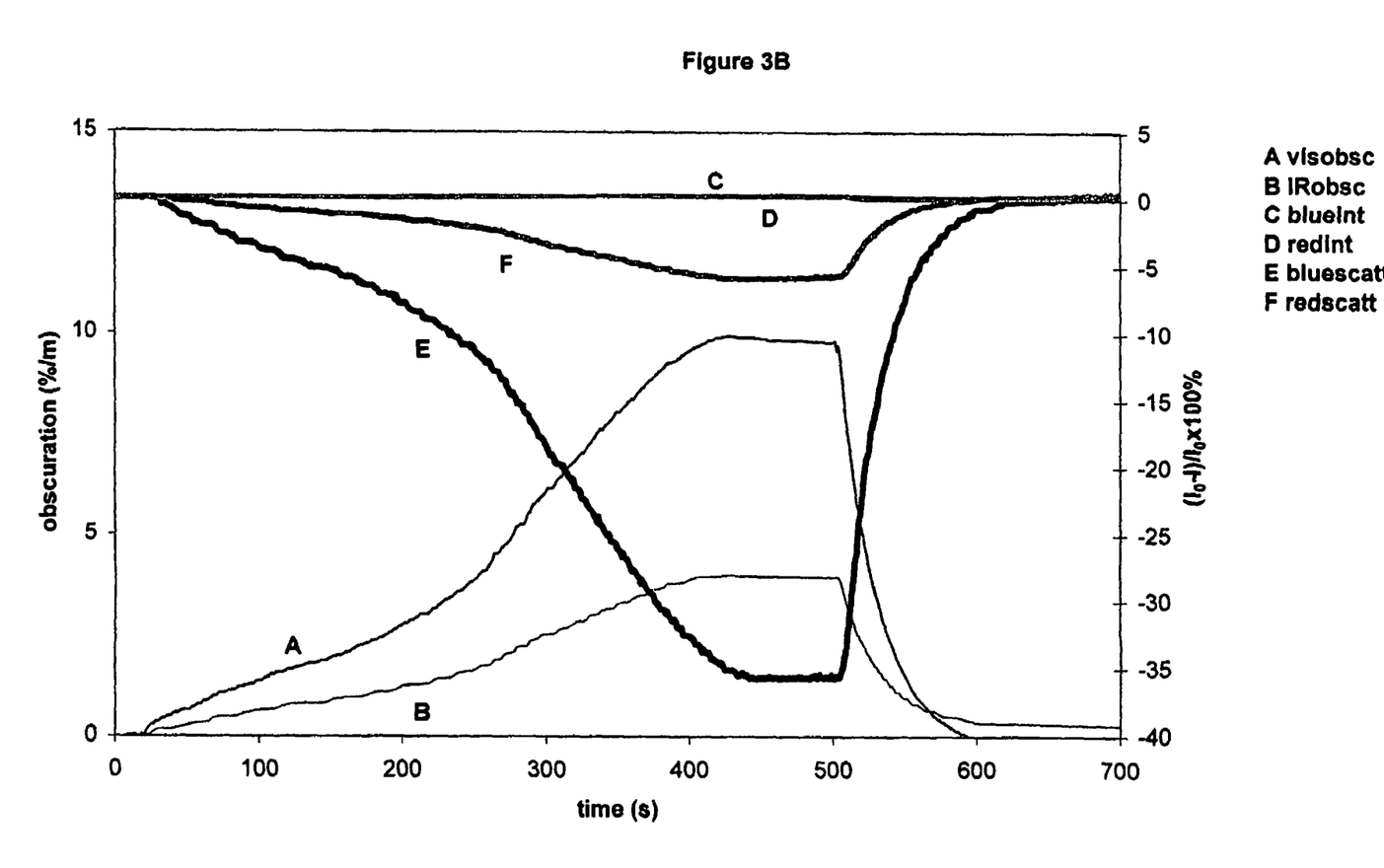
FIG. 3B is a graph showing the data from FIG. 3A re-plotted as the percentage change in the signal from the clean air values.

The signals can all be interpreted as obscuration signals, that is as a percentage change from the background signal in the absence of smoke. The data in FIGS. 3A and 4A has been re-plotted in this way in FIGS. 3B and 4B respectively. The infrared obscuration has also been included in these Figures. The scattering signals, in these plots, become negative obscurations because there has been an increase in the signal rather than a decrease. The patterns seen in FIGS. 3B and 4B are noticeably different and were reproduced with other white and black smokes.

Figure 4B:
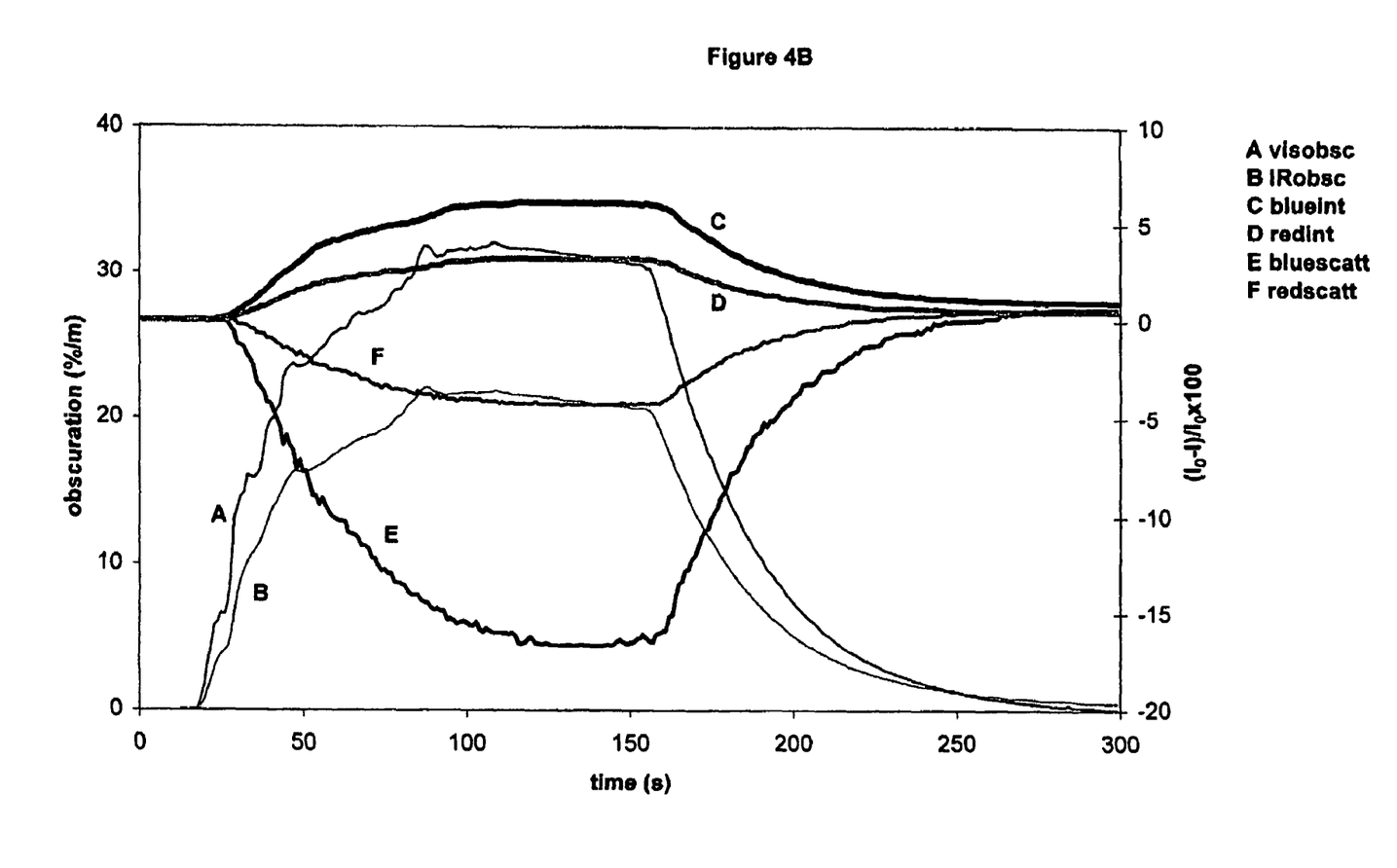
FIG. 4B is a graph showing the data from FIG. 4A re-plotted as the percentage change in the signal from the clean air values.
Figure 5:
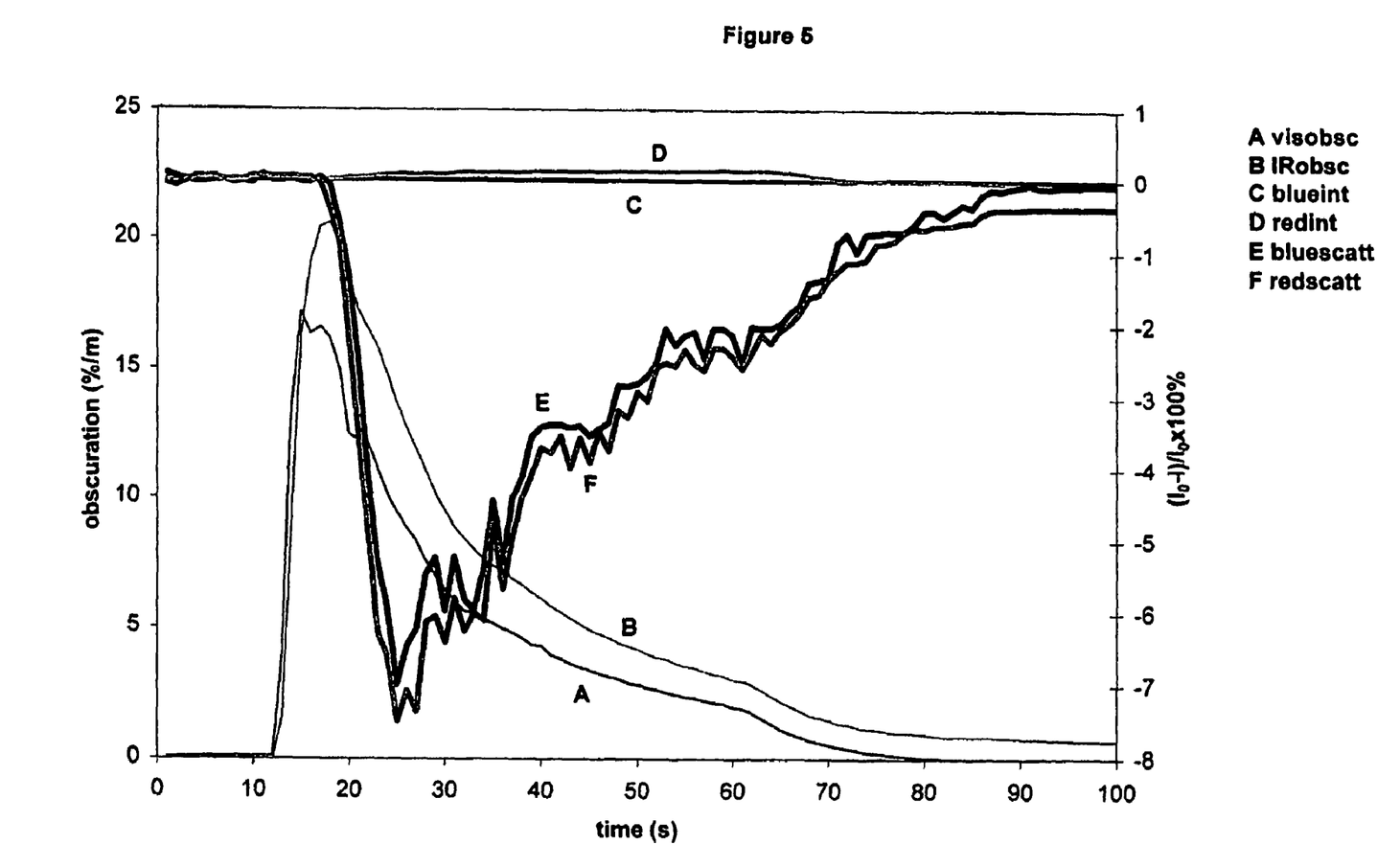
FIG. 5 is a graph showing detector signals, as the percentage change in signal compared to the clean air value, for a maize starch dust aerosol compared to obscuration meter values.

FIG. 5 shows detector signals (interpreted, like FIGS. 4A and 4B, as the percentage change in signal compared to the clean air value) for a (non-smoke) maize starch dust aerosol (plotted against the right hand axis) compared to obscuration meter values (plotted against the left hand axis).

Figure 6:
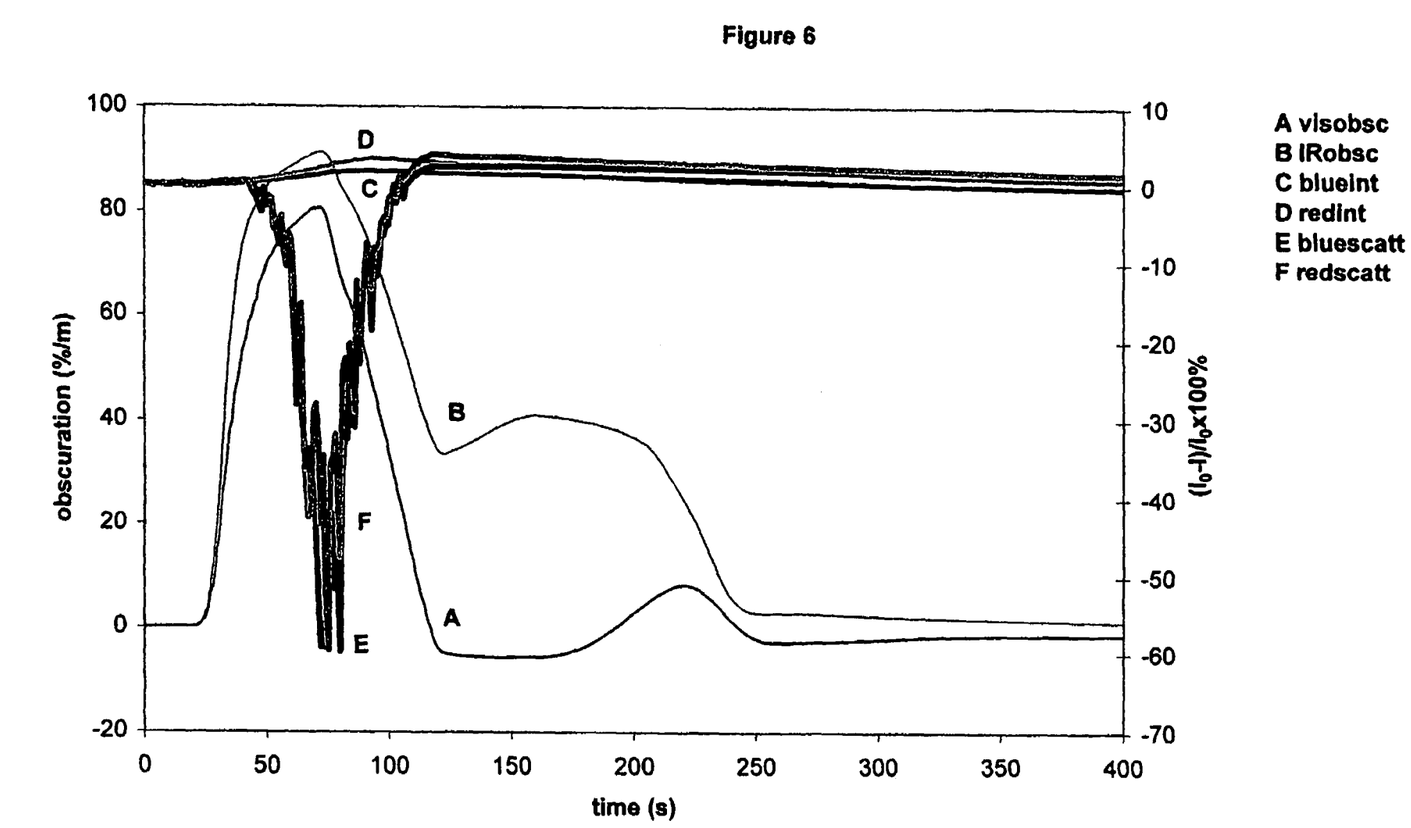
FIG. 6 is a graph showing detector signals, as the percentage change in signal compared to the clean air value, for a water mist aerosol compared to obscuration meter values.

FIG. 6 shows detector signals (again interpreted, like FIGS. 4A and 4B, as the percentage change in signal compared to the clean air value) for a water mist aerosol (plotted against the right hand axis) compared to obscuration meter values (plotted against the left hand axis).

It can be seen from FIGS. 5 and 6 that non-smoke aerosols produced somewhat different patterns as compared with the patterns produced for smoke (FIGS. 4A and 4B). In particular, the relationship between the blue and infrared signals, for both the integrating and scattering detectors, in response to non-smoke aerosols is significantly different from that relationship in response to smoke particles. More specifically, the infrared signals are greater, relative to the blue signals, in response to non-smoke particles than is the case in response to smoke particles. The integrating detector obscuration values for the infrared signal are, in both cases consistently higher than the blue values even though the values are small. The scatter detector signals are almost the same.

Figure 7:
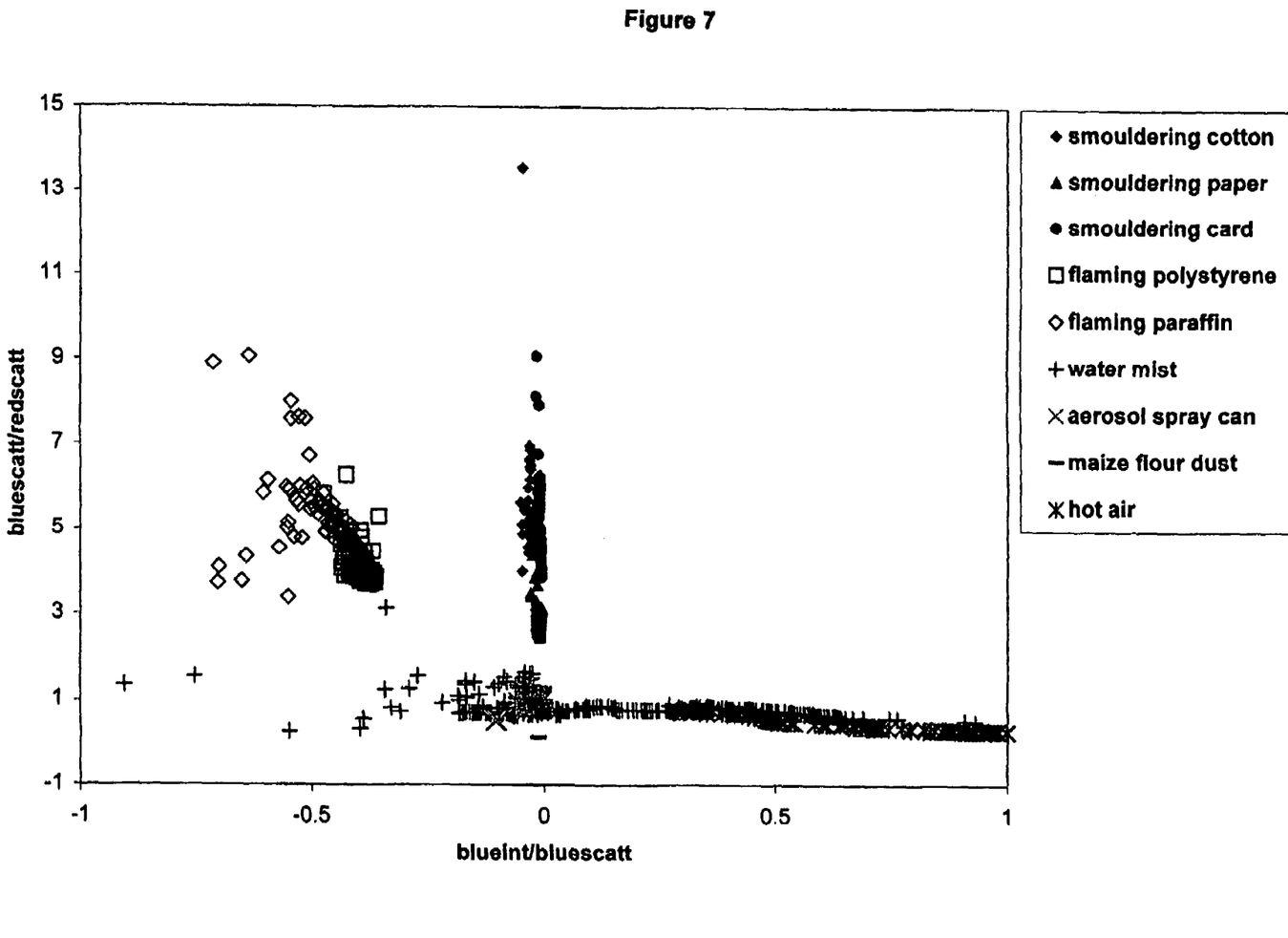
FIG. 7 shows collected date plotted as the blue to infrared scatter signal ration against the blue integrating detector to blue scatter detector signal ratio.

The results for all the tests carried out can be summarised by plotting various ratios of the four detector signals. FIG. 7 shows the plot obtained when the ratio of the blue to infrared scatter signals is plotted against the ratio of the blue integrating detector signal to the blue scatter detector signal. The signals used in both ratios were the percentage change from the clean air signal. These changes can be positive or negative, depending on whether the absorption or scattering predominates, therefore the ratios can also be positive or negative. In FIG. 7, the white or grey smoke data from smouldering fires are solid shapes, the black smoke data from flaming fires are hollow shapes and the non-smoke aerosol data are black or grey crosses or lines. The data plotted for the non-smoke aerosols was all the data recorded where either the integrated blue signal or the scatter blue signal had changed by more than 0.5% from the initial, clean air value. For the smoke aerosols the same condition was applied except that data was only plotted while the smoke density was increasing. It is clear, from FIG. 7, that the aerosols can be classified as black smoke, white smoke or non-smoke, from their position on this plot. Also included in FIG. 7 is data recorded while the air temperature inside the smoke box was increased by blowing in hot air. These data points fell within the region occupied by the non-smoke aerosols.

Other ratios of detector signals can be plotted and, for discriminating some smoke and false alarm aerosols, may be advantageous.

The results discussed above show that white or grey smokes that scatter but do not absorb light have little effect on the integrating detector signal but that they can be detected readily by the scattering detector signal. Also, the light absorbing black smokes have a significant effect on the integrating detector signal. They also, however, affect the scattering detector signal. Thus, in absolute terms, this device has not made a photoelectric detector significantly more sensitive to black smoke but it has made it relatively easy to identify when black smoke is present. There is, therefore, the possibility of changing the threshold of alarm for this case, so that more uniform smoke sensitivity, in terms of the level of obscuration which produces an alarm, can be obtained for black and white smokes.

In all the smoke tests, the signal changes from the blue channel were greater than on the red channel for the scatter detector 9 signals and the integrating detector 5 signals. It was not obvious that it would be the case for the integrating detector signals, where scattering contributes less to the signal. There may be several reasons for this. The scattered signal, although small, may still be the dominant effect particularly for white smokes where other effects are small. For black smokes, where there is significant absorption, the absorption in the blue may be higher than in the infrared or, alternatively, the white coating on the integrating sphere may work better in the blue giving a longer effective absorption path length. It is known, from the obscuration meter data, that the total of the scatter, reflection and absorption losses are higher in the visible than in the infrared region but the absorption component of this cannot be simply determined.

The apparent path length for absorption in the integrating sphere can be estimated by comparing the measured integrating sphere obscuration with the visible obscuration meter data. If the geometric absorption length is taken as twice the sphere diameter, i.e. 100 mm, the apparent absorption length for black smoke is about 150 mm for the blue signal and 80 mm for the infrared signal. These results may be improved with better coatings on the sphere. However, they are not unreasonable given that the integrating sphere is only sensitive to the absorption contribution to the conventional obscuration reading and the sphere is not complete due to the addition of the scattering detector and smoke access apertures. Nevertheless, for the blue signal, it does mean that the integrating sphere is a simple way of obtaining an absorption path length that is longer than a double pass across the smoke chamber, with no critical optical alignment. This may provide better discrimination of different smoke types because the integrating sphere is particularly sensitive to absorption. The apparent absorption path length may vary with contamination of the sphere surface. However, only absorbing contamination should have a marked effect. Contamination which only scatters light will not have a large effect, unlike its effect on conventional optical systems. It may be advantageous to make the scattering properties of the sphere surface non-optimal, as manufactured, so that there is less change induced by contamination with time.

If the minimum threshold for producing an alarm is set at a blue signal change of 1%, which may not be unreasonable as the discrimination data appears to be reliable above 0.5%, the obscurations levels which produce alarms for various smoke particles are listed in the Table below. Also listed in the Table are values for the non-smoke aerosols where the obscuration levels quoted would not be alarms but values where a discrimination decision would be taken. In all the smoke tests, the 1% signal change occurred on the scattering detector first. On the aerosol spray can test, the 1% signal change occurred on the integrated blue signal first. The values quoted in the Table are from the measured data, and they make no allowance for the fact that the smoke density at the detector lags that at the obscuration meters because of the smoke transit time. The values in the Table are therefore minimum sensitivity values. The smoke transit time has more effect on the black smoke obscurations as the rate of rise of smoke density was greater in these tests.

Table of obscuration values measured when a blue signal change of 1% was recorded.

| Aerosol source (type) | Visible obscuration (%/m) | Infrared obscuration (%/m) |
| --- | --- | --- |
| Smouldering cotton (white) | 0.6 | 0.2 |
| Smouldering paper (white) | 1.3 | 0.6 |
| Smouldering card (white) | 4.2 | 1.3 |
| Flaming polystyrene (black) | 14.0 | 8.2 |
| Flaming paraffin (black) | 5.8 | 4.3 |
| Condensed water mist (non-smoke) | 66.8 | 83.2 |
| Aerosol spray can (non-smoke) | 3.2 | 5.6 |
| Maize starch dust (non-smoke) | 12.5 | 18.4 |

The data in the Table indicates that the signal change at alarm condition could be relaxed for the standard smouldering cotton test smoke for conventional smoke detector sensitivity while maintaining a sensitive alarm for black smokes to improve the uniformity of response. Increasing the white smoke alarm threshold also has the effect of making the sensitivity to the different white smokes more uniform, as some of the variance in the Table is due to differences in the rate of rise of the smoke density. If the smouldering cotton alarm is set at about 6%/m, to match the flaming paraffin sensitivity, then the smouldering paper and smouldering card alarms would occur at 9 and 10%/m respectively.

Other smoke types may be identified as providing specific detector signal ratios and be assigned their own alarm conditions.

The use of the four available signals for alarm generation, and the use of signal ratios, provides some compensation for, or recognition of, environmental effects and long term changes in the device, such as caused by contamination of the sphere surface. For instance, the effect of a temperature change is significantly different from that of a smoke aerosol.

Advantages of the embodiment described include: the enhanced sensitivity to absorption, increasing the discrimination between black and white smoke; the ability to make measurements at two or more wavelengths and use the signal ratios for smoke/non-smoke discrimination; and increased absorption path length with no optical components and critical alignment.

From the discussion above, it will be appreciated that the presence of different smoke and particle types can be identified from the four values derived from the detectors 5 and 9: "blueint" and "redint", indicating blue and infrared radiation received by the integrating detector 5, and "bluescatt" and "redscatt" indicating blue and infrared radiation received by the scatter detector 9.

The data from FIG. 7 can be used to set a series of value ranges for "blueint", "redint", "bluescatt" and "redscatt" indicative of black smoke from flaming materials and white/grey smoke from smouldering materials. The values of "blueint", "redint", "bluescatt" and "redscatt" received from the smoke detector 1 can be compared to these ranges by a computer program running on computer 27 (or by any other data processing means, whether implemented by hardware or software) to provide an alarm indicative of black or white/grey smoke being present at the detector 1.

The invention claimed is:

1. A particle detector including:
   a chamber having a substantially high reflectivity substantially Lambertian surface and a radiation absorbing surface, and for receiving particles,
   radiation emitting means for emitting radiation into the chamber and directly irradiating the substantially high reflectivity substantially Lambertian surface, and
   radiation detecting means for detecting the effect of the particles on the radiation within the chamber,
   wherein the radiation detecting means is primarily for detecting absorption of the radiation by the particles,
   wherein the radiation detecting means has a wide viewing angle to receive radiation directly from a substantial portion of the high reflectivity Lambertian surface,
   wherein the radiation detecting means is located at the radiation absorbing surface, and
   wherein the detector further includes a second radiation detecting means primarily for detecting scattering of radiation by the particles, and wherein the second radiation detecting means is sensitive substantially only to radiation in a path between the second radiation detecting means and the radiation absorbing surface.

2. A detector according to claim 1, wherein the particles include smoke particles.

3. A detector according to claim 2, including a second radiation detecting means primarily for detecting scattering of radiation by the particles, and processing means for analysing data from the two radiation detecting means to determine characteristics of the smoke particles in the chamber.

4. A detector according to claim 2, including a second radiation detecting means primarily for detecting scattering of radiation by the particles, and processing means for analysing the data from the two radiation detecting means to determine whether smoke particles or other particles are present in the chamber.

5. A detector according to claim 1, wherein the high reflectivity Lambertian surface is a majority of the chamber surface.

6. A particle detector according to claim 5, wherein the high reflectivity Lambertian surface covers at least 80% of the chamber surface.

7. A detector according to claim 1, including a second radiation emitting means for emitting radiation into the chamber, the second radiation emitting means emitting radiation having a wavelength or wavelengths different from the wavelength or wavelengths of the radiation emitted by the first-mentioned radiation emitting means.

8. A detector according to claim 7, wherein the first-mentioned radiation emitting means emits blue light and the second radiation emitting means emits infrared radiation.

9. A detector according to claim 7, including means for processing signals from the radiation detecting means to obtain data indicative of the detected radiation emitted by the radiation emitting means.

10. A detector according to claim 9, wherein the data is obtained by frequency division multiplexing.

11. detector according to claim 9, wherein the data is obtained by time division multiplexing.

12. A detector according to claim 1, wherein the radiation absorbing surface is black.

13. A detector according to claim 1, wherein the chamber includes holes for allowing the admission of particles, at least one of the holes being in the radiation absorbing surface.

14. A detector according claim 1, wherein the radiation emitting means is positioned arbitrarily with respect to the radiation detecting means.

15. A detector according to claim 1, wherein the radiation emitting means has a beam spread of between about + or −10° and about + or −15°.

16. A detector according to claim 1, wherein the radiation detecting means and the chamber are configured such that the radiation detecting means has a direct view of substantially the entire chamber.

17. A detector according to claim 1, wherein the chamber is ellipsoidal.

18. A detector according to claim 1, wherein the chamber is spherical.

19. A detector according to claim 1, wherein the chamber is an integrating sphere.

20. A particle detector according to claim 1, wherein the Lambertian surface reflects greater than 90% of said radiation.

21. A particle detector including:
a chamber having a substantially high reflectivity substantially Lambertian surface and for receiving particles,
radiation emitting means for emitting radiation into the chamber, and
radiation detecting means for detecting the effect of the particles on the radiation within the chamber,
wherein the radiation detecting means is primarily for detecting absorption of the radiation by the particles, and
wherein the radiation detecting means has a wide viewing angle to receive radiation directly from a substantial portion of the high reflectivity Lambertian surface;
a second radiation emitting means for emitting radiation into the chamber, the second radiation emitting means emitting radiation having a wavelength or wavelengths different from the wavelength or wavelengths of the radiation emitted by the first-mentioned radiation emitting means;
means for processing signals from the radiation detecting means to obtain data indicative of the detected radiation emitted by the radiation emitting means;
wherein the two radiation emitting means are driven at different frequencies and the processing means includes lock-in amplifiers operative at the different frequencies and for receiving the output of the detecting means.

22. A particle detector including:
a chamber having a substantially high reflectivity substantially Lambertian surface and for receiving particles,
radiation emitting means for emitting radiation into the chamber, and
radiation detecting means for detecting the effect of the particles on the radiation within the chamber,
wherein the radiation detecting means is primarily for detecting absorption of the radiation by the particles, and
wherein the radiation detecting means has a wide viewing angle to receive radiation directly from a substantial portion of the high reflectivity Lambertian surface;
a second radiation emitting means for emitting radiation into the chamber, the second radiation emitting means emitting radiation having a wavelength or wavelengths different from the wavelength or wavelengths of the radiation emitted by the first-mentioned radiation emitting means;
at least one further radiation emitting means, in addition to the first and second radiation emitting means, the further radiation means emitting radiation having a wavelength or wavelengths different from the wavelength or wavelengths of the first or second radiation emitting means.

23. A particle detecting method including the steps of:
providing a chamber having a substantially high reflectivity substantially Lambertian surface and a radiation absorbing surface, and for receiving particles,
emitting radiation into the chamber so as to directly irradiate the substantially high reflectivity substantially Lambertian surface, and
detecting the effect of the particles on the radiation within the chamber;
wherein the step of detecting radiation includes detecting the absorption of radiation by receiving radiation directly from a substantial portion of the high reflectivity Lambertian surface using a first radiation detector located at the radiation absorbing surface; and
wherein the step of detecting radiation further includes the step of detecting the scattering of radiation using a second radiation detector that is sensitive substantially only to radiation in a path between the second radiation detector and the radiation absorbing surface.

24. A method according to claim 23, wherein the particles are smoke particles.

25. A method according to claim 23, wherein the step of emitting radiation includes the steps of emitting radiation at two different wavelengths or wavelength ranges.

26. A method according to claim 25, wherein one of said wavelengths or wavelength ranges corresponds to that of blue light and the other of the wavelengths or wavelength ranges corresponds to that of infrared radiation.

27. A method according to claim 25, including the step of analysing the detected radiation to obtain data indicative of the radiation received at each of the wavelengths or wavelength ranges.

28. A method according to claim 27, including the step of deriving from said data signals indicative of the type of particles within the chamber.

29. A method according to claim 28, including the step of deriving signals indicative of whether or not the particles are smoke particles.

30. A method according to claim 23, wherein the Lambertian surface reflects greater than 90% of said radiation.

31. A particle detecting method including the steps of:
providing a chamber having a substantially high reflectivity substantially Lambertian surface and for receiving particles,
emitting radiation at two different wavelengths or wavelength ranges into the chamber, and
detecting the effect of the particles on the radiation within the chamber;
wherein the step of detecting radiation includes detecting the absorption of radiation by receiving radiation directly from a substantial portion of the high reflectivity Lambertian surface;
analysing the detected radiation to obtain data indicative of the radiation received at each of the wavelengths or wavelength ranges; and
emitting radiation of at least a further wavelength or wavelength range, different to said two wavelengths or wavelength ranges.

32. A particle detector including:
a chamber having substantially high reflectivity substantially Lambertian surface and a radiation absorbing surface, and for receiving particles,
radiation emitting means for emitting radiation into the chamber and directly irradiating the substantially high reflectivity substantially Lambertian surface, and
radiation detecting means for detecting the effect of the particles on the radiation within the chamber,
wherein the radiation detecting means is primarily for detecting absorption of the radiation by the particles,
wherein the radiation detecting means has a wide viewing angle to receive radiation directly from a substantial portion of the high reflectivity Lambertian surface,
wherein the radiation detecting means and the chamber are configured such that the radiation detecting means has a direct view of substantially the entire chamber,
wherein the radiation detecting means is located at the radiation absorbing surface, and
wherein the detector further includes a second radiation detecting means primarily for detecting scattering of radiation by the particles, and wherein the second radiation detecting means is sensitive substantially only to radiation in a path between the second radiation detecting means and the radiation absorbing surface.

33. A particle detecting method including the steps of:
providing a chamber having a substantially high reflectivity substantially Lambertian surface and a radiation absorbing surface, and for receiving particles,
emitting radiation into the chamber so as to directly irradiate the substantially high reflectivity substantially Lambertian surface, and
detecting the effect of the particles on the radiation within the chamber using radiation detecting means, the radiation detecting means and the chamber being configured such that the radiation detecting means has a direct view of a region comprising substantially the entire chamber,
wherein the step of detecting radiation includes detecting the absorption of radiation by receiving radiation directly from said region,
wherein the radiation detecting means is located at the radiation absorbing surface, and
wherein the detector further includes a second radiation detecting means primarily for detecting scattering of radiation by the particles, and wherein the second radiation detecting means is sensitive substantially only to radiation in a path between the second radiation detecting means and the radiation absorbing surface.

* * * * *